United States Patent [19]

Reinhard

[11] 4,389,342

[45] Jun. 21, 1983

[54] SYNTHETIC HORMONE-LIKE PEPTIDES AND METHOD FOR THEIR SYNTHESIS

[75] Inventor: Friedrich Reinhard, Munich, Fed. Rep. of Germany

[73] Assignee: Perignon Investments, Ltd., Georgetown, Cayman Islands

[21] Appl. No.: 256,695

[22] Filed: Apr. 23, 1981

Related U.S. Application Data

[63] Continuation-in-part of Ser. No. 136,670, Apr. 2, 1980, which is a continuation-in-part of Ser. No. 82,738, Oct. 9, 1979, abandoned, which is a continuation-in-part of Ser. No. 50,408, Jun. 20, 1979, abandoned, which is a continuation-in-part of Ser. No. 916,874, Jun. 19, 1978, abandoned.

[51] Int. Cl.³ .......................................... C07C 103/52
[52] U.S. Cl. ............................................. 260/112.5 R
[58] Field of Search ................................ 260/112.5 R

[56] References Cited

PUBLICATIONS

Swan, Nature vol. 1199 No. 4893 (1963). 611–612.
Swan, The American Naturalist 103, (1969), 247–257.
Hollenberg, et al. J. Biochem. 104 (1967), 122–127.

Primary Examiner—Delbert R. Phillips
Attorney, Agent, or Firm—Sherman & Shalloway

[57] ABSTRACT

This invention provides a new class of hormone-like peptides having the following sequence:

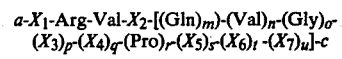

$a\text{-}X_1\text{-Arg-Val-}X_2\text{-}[(Gln)_m\text{-}(Val)_n\text{-}(Gly)_o\text{-}(X_3)_p\text{-}(X_4)_q\text{-}(Pro)_r\text{-}(X_5)_s\text{-}(X_6)_t\text{-}(X_7)_u]\text{-}c$ wherein the definitions for the various substituents and amino acids are given in the specification. The peptide is synthesized by a method which comprises protecting the amino group of the amino acids; forming a metal salt of the protected amino acid at the beginning of the sequence; coupling the salt to a resin; coupling the amino acids in sequence to the resin to form the peptide; cleaving the formed peptide from the resin; removal of the remaining protecting groups; and final purification of the synthesized peptide by either extraction and gel-filtration or Biogel P2-500. The peptides, some of which have also been extracted from the brains of estivating lungfish Protopterus annectens (Owen), have biological activity. The longer chain length peptides, e.g., 11–13 amino acids, which have been isolated from the lungfish, have antimetabolic activity, such as lowering oxygen consumption and lowering body temperature. All of the peptides have been shown to be able to suppress DNA synthesis in cells.

5 Claims, No Drawings

SYNTHETIC HORMONE-LIKE PEPTIDES AND METHOD FOR THEIR SYNTHESIS

RELATED APPLICATIONS

This application is a continuation-in-part of application Ser. No. 136,670, filed Apr. 2, 1980, which in turn is a continuation-in-part of application Ser. No. 082,738, filed Oct. 9, 1979, which in turn is a continuation-in-part of application Ser. No. 050,408, filed June 20, 1979, which in turn is a continuation of application Ser. No. 916,874, filed June 19, 1978, the latter three applications being abandoned.

BACKGROUND OF THE INVENTION

This invention relates to synthetic and natural hormone-like peptides, to a method for their synthesis, and to their biological utility. More specifically, this invention relates to a new class of biologically active hormone-like peptides having a sequence of from 4-13 amino acids.

In copending application Ser. No. 136,670, filed Apr. 2, 1980, the disclosure of which is incorporated herein by reference, a hormone-like peptide having the following sequence is disclosed:

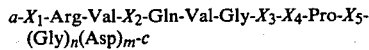

wherein
a is a member of the group consisting of a free amino group and an acylated amino group;
$X_1$ is a member of the group consisting of Ser, Gln, Glu, and Pyr-Glu;
$X_2$ is a member of the group consisting of Lys and Ser;
$X_3$ is a member of the group consisting of Ser and Asn;
$X_4$ is a member of the group consisting of Ser, Gln and Lys;
$X_5$ is a member of the group consisting of Gln and Ser;
c is a member of the group consisting of a free acid group and an acid amide group;
n=0 or 1, and
m=0 or 1, provided that when N=0, m=0;
Pyr-Gln being pyrrolidyl glutamic acid.

The above-mentioned peptides, which have previously been extracted from brains of estivating lungfish *Protopterus annectens* (Owen) by the procedures described in Ser. No. 136,670, have been found to possess antimetabolic activity. For example, when injected intravenously into test animals, the peptide causes hypothermia, i.e., reduction in body temperature. It has also been found that the peptide causes the oxygen consumption and respiration rate of test animals (rats and mice) to be lowered. Using cultures of living cells from hamsters and liver cells from the rat, it has been found that protein biosynthesis and DNA-synthesis were lowered, causing a slowdown in cell division. Furthermore, the peptide has been found to be non-toxic since its effects are reversible. Tests also show that the peptide is non-species specific, i.e., it works in animals other than that which produces it.

As disclosed in the above-mentioned copending application, the peptide is extracted from the brains of estivating (sleeping), lungfish, *Protopterus annectens* (Owen). Such a species of lungfish is found in the Chad basin in Central Africa. However, since a large number of estivating lungfish must be sacrificed in order to yield a small amount of the peptide, there is a need for a process whereby the peptides can be synthesized in large quantities using off-the-shelf chemicals.

Efforts by the inventor to synthesize the 11-13 amino acid sequence peptide described above have not only been successful, but in addition, have led to the discovery of additional biologically-active peptides which are closely structurally related to the lungfish-derived peptides, but which have not been found in the lungfish. These synthetic hormone-like peptides have been shown to possess similar biological activity as the lungfish-derived peptides and, in some cases, greater activity.

Furthermore, biological activity, particularly DNA-biosynthesis in living cells, has been found in the synthetically derived peptide chains of as few as four amino acids.

SUMMARY OF THE INVENTION

The present invention provides synthetic hormone-like peptides (tetrapeptides or tridecapeptides) having the following formula:

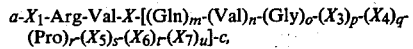

wherein
$X_1$–$X_7$ are each, independently, an amino acid;
a is a free amino group or an acylated amino group;
c is a free acid group or an acid amide group;
m, n, o, p, q, r, s, t and u are all integers of 0 or 1 with the proviso that $m \geq n \geq o \geq p \geq q \geq r \geq s \geq t \geq u$.

The present invention also provides a method of synthesizing these peptides having from 4 to 13 amino acids. The method comprises protecting the $\alpha$-$NH_2$ groups of the amino acids from which the peptide is formed, the side chains of lysine and arginine, and the hydroxyl group of serine; preparing a metal salt of the first glutamine in the peptide chain (for the peptides of five or more amino acid chain lengths, or where either $X_1$ or $X_2$ is a glutamine), the $\alpha$-$NH_2$ group of glutamine being blocked by a protecting group; coupling the glutamine salt to a resin; coupling in sequence the protected amino acids using a coupling agent and a 3- to 6-fold excess of the inactivated amino acid to form the product peptide; and cleaving the peptides so formed from the resin and thereafter removing protecting groups.

DETAILED DESCRIPTION OF THE INVENTION

According to the present invention, synthetic peptides having from 4 to 13 amino acid sequences (i.e., tetrapeptides to tridecapeptides) of the following formula are provided:

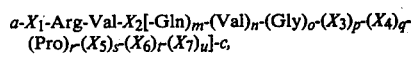

wherein,
$X_1$–$X_7$ are each, independently of each other, an amino acid selected from the alpha-amino carboxylic acids, and pharmacologically active derivatives thereof,
a is a member of the group consisting of a free amino group and an acylated amino group;

c is a member of the group consisting of a free carboxylic acid group, a carboxylic acid amino group, and a carboxylic acid ester group;

m, n, o, p, q, r, s, t and u are integers of 0 or 1, with the proviso that $m \geq n \geq o \geq p \geq q \geq r \geq s \geq t \geq u$.

This proviso means that for peptide chain lengths of less than 13 amino acids, the amino acids are eliminated consecutively, beginning at the C-terminus.

Accordingly, the present invention includes within its scope, the biologically active tetra- or trideca-peptides of the formula:

| | |
|---|---|
| a-$X_1$—Arg—Val—$X_2$—c | (I) |
| a-$X_1$—Arg—Val—$X_2$—Gln—c | (II) |
| a-$X_1$—Arg—Val—$X_2$—Gln—Val—c | (III) |
| a-$X_1$—Arg—Val—$X_2$—Gln—Val—Gly—c | (IV) |
| a-$X_1$—Arg—Val—$X_2$—Gln—Val—Gly—$X_3$—c | (V) |
| a-$X_1$—Arg—Val—$X_2$—Gln—Val—Gly—$X_3$—$X_4$—c | (VI) |
| a-$X_1$—Arg—Val—$X_2$—Gln—Val—Gly—$X_3$—$X_4$—Pro—c | (VII) |
| a-$X_1$—Arg—Val—$X_2$—Gln—Val—Gly—$X_3$—$X_4$—Pro—$X_5$—c | (VIII) |
| a-$X_1$—Arg—Val—$X_2$—Gln—Val—Gly—$X_3$—$X_4$—Pro—$X_5$—$X_6$—c | (IX) |
| a-$X_1$—Arg—Val—$X_2$Gln—Val—Gly—$X_3$—$X_4$—Pro—$X_5$—$X_6$—$X_7$—c | (X) |

The abbreviations for the various amino acid residues are standard and, for convenience, are tabulated below:

| Abbreviation | Amino Acid |
|---|---|
| Ala | Alanine |
| Arg | Arginine |
| Asn | Asparagine |
| Asp | Aspartic acid |
| Cys | Cystine (half) |
| Glu | Glutamic acid |
| Gln | Glutamine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Pyr | Pyrrolidyl-glutamic acid |
| Ser | Serine |
| Thr | Threonine |
| Trp | Tryptophan |
| Tyr | Tyrosine |
| Val | Valine |

The amino acids can be selected in the D-, L-, or DL-stereo-configuration, or may be optically inactive. Preferred amino acids for the groups $X_1$–$X_5$ include arginine, asparagine, glutamine, glycine, glutamic acid, histidine, lysine, phenylalanine, proline, serine, tryptophane, tyrosine, valine, and pyrrolidyl glutamic acid. In particular, preferred amino acids for $X_1$ include Gln, Phe, Pyr, Ser, Trp, Tyr, Glu;
for $X_2$: His, Lys, Phe, Pro, Ser, Tyr;
for $X_3$: Asn, His, Phe, Pro, Ser, Tyr;
for $X_4$: Gln, His, Lys, Phe, Pro, Ser, Tyr;
for $X_5$: Asn, Gln, Ser;
for $X_6$: Gly; and
for $X_7$: Asp.

Among the tetra- or trideca-peptides of formula (I)–(X), the decapeptides of formula (VIII), which include the peptides isolated from the lungfish *Protopterus annectens* (Owen), and analogs thereof, especially those in which $X_1$=Pyr; $X_2$=Lys, Phe or Tyr; $X_3$=Ser; $X_4$=Ser; and $X_5$=Gln; and the nonapeptides of formula (VII), where $X_1$=Pyr; $X_2$=Lys; $X_3$=Ser; and $X_4$=Ser; have been found to be particularly active with regard to their ability to suppress DNA-synthesis in living cells. Moreover, relative to the activity of the decapeptide isolated from the lungfish, most of the tetrapeptide to decapeptide analogs in which $X_1$=Phe or Pyr; and $X_2$=Lys; showed about 50% activity in suppressing DNA synthesis.

The method for synthesizing the above-mentioned peptides involves the coupling of amino acids by reaction of the carboxyl function of one with the amino function of another to produce an amide linkage. However, in order to achieve effective coupling, it is desirable that all reactive functionalities not participating directly in the reaction be protected by the use of appropriate blocking groups and that the carboxyl function which is to be coupled be appropriately unblocked to permit coupling to proceed. This involves a careful selection of both reaction sequence and reaction conditions as well as utilization of specific blocking groups so that the desired peptide product will be realized.

In practice, synthesis can begin at either end of the amino acid chain, i.e., at the free amino acid or acylated amino group a, or the carboxylic acid or carboxylic acid amide group c. However, it is preferred to begin the synthesis of the peptide at the free carboxylic acid or acid amide group terminus, e.g., with amino acid $X_5$ for the peptides of formula (VIII).

Accordingly, as the initial step, the alpha-$NH_2$-groups are protected with a blocking group such as t-butyloxycarbonyl (BOC). Other blocking groups which can be used include benzyloxycarbonyl (CBZ), t-amyloxycarbonyl (AOC), p-methoxybenzyloxycarbonyl (MBOC), adamatyloxycarbonyl (AdOC), and isobornyloxycarbonyl. In addition, blocking groups such as 2-Cl-carbobenzoxy (2-Cl-Z) and 2-nitrocarbobenzoxy (2-NO-Z) can be used to protect the $\epsilon$-$NH_2$ group in lysine and arginine, respectively. The hydroxyl group of serine can be protected by such a blocking group as 0-benzyl ether (Bzl). These blocking agents are known and other blocking agents are described, for example, in U.S. Pat. Nos. 4,217,268, 4,199,500, 4,209,426, 4,206,199 and any of the blocking agents disclosed in these patents can also be used in the synthesis of the novel hormone-like peptides of this invention. After blocking of the amino group of the $X_5$ amino acid, the protected $X_5$ amino acid is coupled to a peptide resin. For instance, when $X_5$ is glutamine, a metal salt of the protected glutamine is prepared. As an example, the cesium salt of BOC-glutamine is prepared and is coupled to a suitable resin such as 1% cross-linked dichloromethylated polystyrene divinyl benzene.

With the exception of glutamine, the BOC-amino acids are linked to the BOC-glutamine-coupled resin in the sequence shown above using N,N'-dicyclohexylcarbodiimide (DCC) as a coupling agent to activate the free carboxyl function, thereby permitting coupling to proceed. Typically, a 3- to 6-fold, preferably 6-fold, excess of the BOC-amino acid is used in each coupling step. After each coupling step, the blocked α-NH$_2$ group is deprotected by treating the resin with 50% TFA in CH$_2$Cl$_2$.

After the complete peptide has been obtained, the peptide is cleaved from the resin by treating the peptide with a mixture of anhydrous hydrogen bromide in TFA. The cleavage comprises contacting the peptide-carrying resin with the TFA and hydrogen bromide at room temperature (20°-25° C.) for a period of from 90 to 120 minutes, preferably 120 minutes. As to the nitro-group coupled to arginine, it may be removed by catalytic hydrogenolysis in the presence of a catalyst such as palladium on carbon.

In an alternative method, the synthetic peptide can be synthesized using the same protected amino acids as mentioned above, but instead of using a coupling agent, the carboxylic acid function can be converted to an active form, e.g., active ester derivative, active azide derivative, active symmetrical or mixed anhydride derivative, etc.

Preferably, in this alternative procedure, coupling is achieved by converting the carboxyl function to its active ester derivative. Useful esters include, for example, 2,4,5-trichlorophenylester, pentachlorophenylester, and p-nitrophenylester. After sequential coupling, the protecting block groups are then deblocked from the peptide by a suitable treatment as described above.

In still another alternative synthesis route, the protecting groups described above are coupled to the amino acids with the exception of arginine where the guanidino group is protected by a p-toluene sulfonyl group (TOS). Thereafter, the protected amino acids are linked as described in the first embodiment. The cleavage of the peptide from the resin is achieved by treating with anhydrous hydrogen fluoride. The TOS group is cleaved from the arginine by contacting the product with sodium in liquid ammonia.

After hydrogenolysis, to cleave the synthesized peptide product from the resin, it is necessary to purify the desired product by removing unreacted salts, protective groups, and other impurities, as well as unreacted amino acids and short sequence peptides, i.e., peptides of less than 11 amino acids in its sequence.

As a first step in the purification, the cleaved product may be precipitated in ether. Final purification by partition chromatography, for example, using Biogel P2-500 column with 0.04% TFA, provides a final product synthetic peptide of sufficiently high purity to give positive results in biological activity tests, e.g., antimetabolic activity such as effecting hypothermia and lowering oxygen consumption in in vivo tests on mice and rats, and suppression of protein bio-synthesis and DNA-synthesis in in vitro CHO cells and rat liver cells. The details of the assay methods for each of these activities is described in great detail in the inventor's copending application Ser. No. 136,670.

For actual pharmaceutical preparations where substantially 100% purity is required, further purification can be obtained by subjecting the purified product from partition chromatography to further separation in high pressure liquid chromatography, for example.

The present invention is further illustrated in the following nonlimiting examples. All of the amino acids capable of existing as stereoisomers are used in the L-form or in the neutral form, except as otherwise noted.

EXAMPLE 1

The peptide having the following formula is prepared:

Ser-Arg-Val-Lys-Gln-Val-Gly-Ser-Ser-Pro-Gln.

The cesium salt of BOC-glutamine is prepared by dissolving 2.5 g of BOC glutamine in 15 ml of ethanol and diluting with 3 ml water. The pH of this solution is adjusted to 7.0 by adding dropwise aqueous cesium hydroxide. This neutral solution is evaporated to dryness. The dry product is dissolved in benzene and again evaporated to dryness. The steps of dissolving in benzine and evaporating to dryness are repeated 3 times. The dry BOC-glutamine is obtained as a white solid and dried over P$_2$O$_5$ for five hours.

The cesium salt of the BOC-glutamine obtained above is dissolved in 30 ml dimethyl formamide and 5 grams of Merrifield peptide resin (1% cross-linked dichloromethylated polystyrene divinyl benzene, purchased from the Pierce Chemical Company) is added to the solution. The mixture is placed in a screw-capped vial and stirred for 15 hours at 50° C. Thereafter, the resin is filtered and washed thoroughly with N,N-dimethylformamide (DMF) and ethanol, after which it is dried. The substitution of the resin is determined by amino acid analysis with an equimolar mixture of concentrated hydrochloric acid and propionic acid at 130° C. for 3 hours. The substitution obtained is 0.66 meq/g resin.

Amino acids used in the synthesis are protected with blocking groups. For the alpha-amino groups, BOC is used as the blocking group. The hydroxyl group of serine is protected as 0-benzyl ether. The ε-NH$_2$ group of lysine is protected with 2-Cl-Z, whereas arginine is used as BOC-nitroarginine.

The BOC-Gln resin is placed in a reaction vessel which is fitted with a glass filter at the bottom. All reaction steps and washings are conducted in this vessel.

The amino acids are coupled using dicyclohexylcarbodiimide as the coupling agent, except for the coupling of glutamine, which is achieved by using BOC-glutamine-p-nitrophenylester. A six-fold excess of the BOC amino acid is used in each step. The synthesis is followed by amino acid analysis after each linkage.

Deblocking of BOC-protecting groups is achieved by treatment with an equimolar mixture of TFA/CH$_2$Cl$_2$ at room temperature for 25 minutes. The NO$_2$-mixture or arginine is removed by catalytic hydrogenolysis in the presence of palladium on carbon.

EXAMPLE 2

The amino groups are protected by the same reagents as used in Example 1. The coupling is achieved by using the active p-nitrophenylesters of each amino acid in the synthesis instead of the dicyclohexylcarbodiimide coupling agent used in Example 1. Cleavage of the blocking groups is conducted in the same manner as described in Example 1.

EXAMPLE 3

The same protecting groups as in Example 1 are used with the exception of arginine where the guanidino group is protected by a p-toluene sulfonyl group (TOS). Coupling is performed in accordance with Example 1. Cleavage of the peptide from the resin is obtained by using anhydrous hydrogen fluoride. The TOS group in the arginine is removed by contacting with sodium in liquid ammonia.

EXAMPLE 4

Example 1 is repeated except that the serine amino terminus is replaced by tyrosine or tryptophan to prepare Tyr-Arg-Val-Lys-Gln-Val-Gly-Ser-Ser-Pro-Gln and Trp-Arg-Val-Lys-Gln-Val-Gly-Ser-Ser-Pro-Gln.

EXAMPLE 5

By the preparatory procedures described above, each of the peptides shown in the following table were synthesized and their metabolic effects, as determined by the effect of the peptide on DNA-synthesis on Chinese hamster ovary cells (CHO) were measured by the following procedure:

1. CHO seed stock obtained from American Type Culture Collection, Rockville, Md. (ATTC) is placed in liquid nitrogen.
2. As needed, new seed is removed from liquid nitrogen, supplied with new Ham's F-12 media which contained 10% Fetal Calf Serum.
3. Plastic plates containing $2-4 \times 10^5$ cells/ml are pre-incubated for 4 hours at 37° C. in an atmosphere containing 0.1% $CO_2$.
4. After pre-incubation, sample of various concentrations of test material are added to the plates. For control purposes, plates containing only Ham's F-12 are used. These plates are then incubated for the desired period of time.
5. After the incubation period, cells are washed five times with 2 mM cold Thymidine and then the cells are killed with 7% trichloracetic acid solution.
6. The dead cells are scraped from the bottom of the plates and filtered through a GFC filter. The thymidine incorporation is measured by liquid scintillation counting.
7. The incorporated thymidine is measured in decompositions per minute and expressed as percent of control.
8. Each test is done with three or more plates of material and then each test is repeated at least three times.

The table also shows the activity on DNA-synthesis, given as a percent of the activity of the peptide isolated and purified from estivating lungfish as described in Example 19 and FIGS. 3 and 4 and Table 6 of application Ser. No. 136,670 (incorporated by reference).

TABLE

| Run No. | $X_1$ | $X_2$ | | | $X_3$ | $X_4$ | $X_5$ | $X_6$ | $X_7$ | Activity on DNA Synthesis (% of activity of natural product) |
|---|---|---|---|---|---|---|---|---|---|---|
| 1 | Pyr— | D-Arg—Val—Lys— | Gln—Val—Gly—Ser—Ser—Pro—Gln— | | | | | | | 110 |
| 2 | Pyr— | Arg—Val—Tyr— | Gln—Val—Gly—Ser—Ser—Pro—Gln | | | | | | | 100 |
| 3 | Pyr— | Arg—Val—Phe— | Gln—Val—Gly—Ser—Ser—Pro—Gln | | | | | | | 100 |
| 4 | Pyr— | Arg—Val—Lys— | Gln—Val—Gly—Ser—Ser—Pro—Gln—$NH_2$ | | | | | | | 90 |
| 5 | Pyr— | Arg—Val—Lys— | Gln—Val—Gly—Ser—Ser—Pro $NH_2$ | | | | | | | 90 |
| 6 | Pyr— | Arg—Val—Lys— | Gln—Val—Gly—Ser—Ser—Pro | | | | | | | 90 |
| 7 | Pyr— | Arg—Val—Lys— | Gln—Val—Gly—Ser—Ser—Pro—Gln | | | | | | | 50 |
| 8 | Pyr— | Arg—Val—Lys— | Gln—Val—Gly—Tyr—Ser—Pro—Gln | | | | | | | 50 |
| 9 | Pyr— | Arg—Val—Lys— | Gln—Val—Gly—Phe—Ser—Pro—Gln | | | | | | | 50 |
| 10 | Pyr— | Arg—Val—Lys— | Gln—Val—Gly—Ser—Tyr—Pro—Gln | | | | | | | 50 |
| 11 | Pyr— | Arg—Val—Lys— | Gln—Val—Gly—Ser—Ser—Pro—Asn | | | | | | | 50 |
| 12 | Phe— | Arg—Val—Lys— | Gln—Val—Gly—Ser—Ser—Pro$NH_2$ | | | | | | | 50 |
| 13 | Pyr— | Arg—Val—Lys— | Gln—Val—Gly—Ser—Ser | | | | | | | 50 |
| 14 | Pyr— | Arg—Val—Lys— | Gln—Val—Gly—Ser | | | | | | | 50 |
| 15 | Pyr— | Arg—Val—Lys— | Gln—Val—Gly | | | | | | | 50 |
| 16 | Pyr— | Arg—Val—Lys— | Gln | | | | | | | 50 |
| 17 | Pyr— | Arg—Val—Lys | | | | | | | | 50 |
| 18 | Pyr— | Arg—Val—Lys— | Gln—Val—Gly—Ser—Phe—Pro—Gln | | | | | | | 40 |
| 19 | Tyr— | Arg—Val—Lys— | Gln—Val—Gly—Ser—Ser—Pro$NH_2$ | | | | | | | 40 |
| 20 | Phe— | Arg—Val—Lys— | Gln—Val—Gly—Ser—Ser—Pro—Gln | | | | | | | 40 |
| 21 | Phe— | Arg—Val—Lys— | Gln—Val—Gly—Tyr—Ser—Pro—Gln | | | | | | | 40 |
| 22 | Phe— | Arg—Val—Lys— | Gln—Val—Gly—Phe—Ser—Pro—Gln | | | | | | | 40 |
| 23 | Phe— | Arg—Val—Lys— | Gln—Val—Gly—Pro—Ser—Pro—Gln | | | | | | | 40 |
| 24 | Phe— | Arg—Val—Lys— | Gln—Val—Gly—His—Ser—Pro—Gln | | | | | | | 40 |
| 25 | Phe— | Arg—Val—Tyr— | Gln—Val—Gly—Ser—Ser—Pro—Gln | | | | | | | 40 |
| 26 | Phe— | Arg—Val—Lys— | Gln—Val—Gly—Ser—Tyr—Pro—Gln | | | | | | | 40 |
| 27 | Phe— | Arg—Val—Lys— | Gln—Val—Gly—Ser—Phe—Pro—Gln | | | | | | | 40 |
| 28 | Phe— | Arg—Val—Lys— | Gln—Val—Gly—Ser—His—Pro—Gln | | | | | | | 40 |
| 29 | Phe— | Arg—Val—Lys— | Gln—Val—Gly—Ser—Ser—Pro—Asn | | | | | | | 40 |
| 30 | Pyr— | Arg—Val—Lys— | Gln—Val | | | | | | | 40 |
| 31 | Pyr— | Arg—Val—Lys— | Gln—Val—Gly—Pro—Ser—Pro—Gln | | | | | | | 30 |
| 32 | Pyr— | Arg—Val—Lys— | Gln—Val—Gly—His—Ser—Gln | | | | | | | 30 |
| 33 | Tyr— | Arg—Val—Lys— | Gln—Val—Gly—Ser—Ser—Pro—Gln | | | | | | | 30 |
| 34 | Tyr— | Arg—Val—Lys— | Gln—Val—Gly—Tyr—Ser—Pro—Gln | | | | | | | 30 |
| 35 | Tyr— | Arg—Val—Lys— | Gln—Val—Gly—Phe—Ser—Pro—Gln— | | | | | | | 30 |
| 36 | Tyr— | Arg—Val—Lys— | Gln—Val—Gly—Pro—Ser—Pro—Gln— | | | | | | | 30 |
| 37 | Tyr— | Arg—Val—Lys— | Gln—Val—Gly—Ser—His—Pro—Gln— | | | | | | | 30 |
| 38 | Tyr— | Arg—Val—Lys— | Gln—Val—Gly—Ser—Ser—Pro—Asn | | | | | | | 30 |
| 39 | Tyr— | Arg—Val—Lys— | Gln—Val—Gly—Ser—Tyr—Pro—Gln— | | | | | | | 25 |
| 40 | Tyr— | Arg—Val—Lys— | Gln—Val—Gly—Ser—Phe—Pro—Gln— | | | | | | | 25 |
| 41 | Tyr— | Arg—Val—Pro— | Gln—Val—Gly—Ser—Ser—Pro—Gln— | | | | | | | 20 |
| 42 | Tyr— | Arg—Val—Lys— | Gln—Val—Gly—His—Ser—Pro—Gln— | | | | | | | 20 |
| 43 | Ser— | Arg—Val—Lys— | Gln—Val—Gly—Ser—Ser—Pro—Gln— | | | | | | | <10 |

TABLE-continued

| Run No. | $X_1$ | $X_2$ | $X_3$ | $X_4$ | $X_5$ | $X_6$ | $X_7$ | Activity on DNA Synthesis (% of activity of natural product) |
|---|---|---|---|---|---|---|---|---|
| 44 | Ser— | Arg—Val—Lys—Gln—Val—Gly—Ser—Ser—Pro—Gln—Gly | | | | | | <10 |
| 45 | Ser— | Arg—Val—Lys—Gln—Val—Gly—Ser—Ser—Pro—Gln—Gly—Asp | | | | | | <10 |
| 46 | Pyr— | Arg—Val—Ser—Gln—Val—Gly—Ser—Lys—Pro—Gln | | | | | | <10 |
| 47 | Pyr— | Arg—Val—Pro—Gln—Val—Gly—Ser—Ser—Pro—Gln | | | | | | <10 |
| 48 | Pyr— | Arg—Val—Pro—Gln—Val—Gly—Pro—Ser—Pro—Gln | | | | | | <10 |
| 49 | Pyr— | Arg—Val—Lys—Gln—Val—Gly—Ser—Pro—Pro—Gln | | | | | | <10 |
| 50 | Pyr— | Arg—Val—Lys—Gln—Val—Gly—Ser—His—Pro—Gln | | | | | | <10 |
| 51 | Tyr— | Arg—Val—Ser—Gln—Val—Gly—Ser—Lys—Pro—Gln | | | | | | <10 |
| 52 | Tyr— | Arg—Val—Tyr—Gln—Val—Gly—Ser—Ser—Pro—Gln | | | | | | <10 |
| 53 | Tyr— | Arg—Val—Phe—Gln—Val—Gly—Ser—Ser—Pro—Gln | | | | | | <10 |
| 54 | Trp— | Arg—Val—Lys—Gln—Val—Gly—Ser—Ser—Pro—Gln | | | | | | <10 |
| 55 | Trp— | Arg—Val—Tyr—Gln—Val—Gly—Ser—Ser—Pro—Gln | | | | | | <10 |
| 56 | Trp— | Arg—Val—Phe—Gln—Val—Gly—Ser—Ser—Pro—Gln | | | | | | <10 |
| 57 | Trp— | Arg—Val—Pro—Gln—Val—Gly—Ser—Ser—Pro—Gln | | | | | | <10 |
| 58 | Trp— | Arg—Val—Lys—Gln—Val—Gly—Ser—Ser—ProNH$_2$ | | | | | | <10 |
| 59 | Try— | Arg—Val—Lys | | | | | | <10 |
| 60 | Phe— | Arg—Val—Lys | | | | | | <10 |
| 61 | Trp— | Arg—Val—Lys | | | | | | <10 |
| 62 | Pyr— | Arg—Val—Tyr | | | | | | <10 |
| 63 | Trp— | Arg—Val—Tyr | | | | | | 0 |
| 64 | Ser— | Arg—Val—Ser—Gln—Val—Gly—Ser—Lys—Pro—Gln | | | | | | 0 |
| 65 | | Gln—Val—Gly—Ser—Ser—Pro—Gln | | | | | | 0 |
| 66 | | Ser—Ser—Pro—Gln | | | | | | 0 |

What I claim is:

1. A hormone-like peptide having antimetabolic activity comprising a peptide of the formula $$a\text{-}X_1\text{-}Arg\text{-}Val\text{-}X_2\text{-}(Gln)_m\text{-}(Val)_n\text{-}(Gly)_o\text{-}(X_3)_p\text{-}(X_4)_q\text{-}(Pro)_r\text{-}(X_5)_s\text{-}c$$

wherein
a is a member of the group consisting of a free amino group and an acylated amino group,
c is a member of the group consisting of a free carboxylic acid group, a carboxylic acid amide group, and a carboxylic acid ester group
$X_1$ is Pyr or Phe,
$X_2$ is Lys, Tyr or Phe,
$X_3$ is Ser, Tyr, or Phe
$X_4$ is Ser or Tyr,
$X_5$ is Gln or Asn, and
m, n, o, p, q, r and s are integers of 0 or 1, with the proviso that $m \geq n \geq o \geq p \geq q \geq r \geq s$; with the further provisos that:
when $X_1$ is Phe then $X_2$ is Lys, $X_3=X_4=$Ser, and $m=n=o=p=q=r=1$ and $s=0$;
when $X_2$ is Tyr or Phe, then $X_3=X_4=$Ser, $X_5=$Gln, and $m=n=o=p=q=r=s=1$;
when $X_3$ is Tyr or Phe, then $X_4$ is Ser, $X_5$ is Gln and $m=n=o=p=q=r=s=1$; and
when $X_4$ is Tyr, then $X_5$ is Gln and $m=n=o=p=q=r=s=1$; and when $n=1$, then $o=1$.

2. The hormone-like peptide of claim 1 having the formula

Pyr-Arg-Val-Lys-Gln-Val-Gly-Ser-Ser-Pro-Gln.

3. The hormone-like peptide of claim 1 having the formula

Pyr-Arg-Val-Tyr-Gln-Val-Gly-Ser-Ser-Pro-Gln.

4. The hormone-like peptide of claim 1 having the formula

Pyr-Arg-Val-Phe-Gln-Val-Gly-Ser-Ser-Pro-Gln.

5. The hormone-like peptide of claim 1 having the formula

Pyr-Arg-Val-Lys-Gln-Val-Gly-Ser-Ser-Pro.

* * * * *